United States Patent [19]
Fischer et al.

[11] Patent Number: 5,977,417
[45] Date of Patent: Nov. 2, 1999

[54] PREPARATION OF 1,4-BUTANEDIOL

[75] Inventors: Rolf Fischer, Heidelberg; Christoph Sigwart, Schriesheim, both of Germany

[73] Assignee: Basf Aktiengesellschaft, Ludwigshafen, Germany

[21] Appl. No.: 09/192,484

[22] Filed: Nov. 17, 1998

Related U.S. Application Data

[62] Division of application No. 08/523,887, Sep. 6, 1995.

[30] Foreign Application Priority Data

Sep. 6, 1994 [DE] Germany .............................. 44 31 743

[51] Int. Cl.$^6$ ..................................................... C07C 27/00
[52] U.S. Cl. ............................................................ 568/861
[58] Field of Search ............................................... 568/861

[56] References Cited

PUBLICATIONS

J. Org. Chem., 1984, 49, pp. 3707–3711.
Houben–Weyl: Methoden der Organischen Chemie, VI/3, pp. 435–441.
Ullmann's Encyclopedia of Industrial Chemistry, 5th Ed., vol. A26, p. 222.
Weissermel–Arpe: Industrielle Organische Chemie, 4, p. 112.

Primary Examiner—Dwayne C. Jones
Attorney, Agent, or Firm—Keil & Weinkauf

[57] ABSTRACT 1,4-Butanediol is prepared by a process which comprises converting 1,3-butadiene diepoxide in the presence of hydrogen over a hydrogenation catalyst whose active component is not elemental Pd and/or Pt. The hydrogenation catalyst preferably contains at least one element from the group Ib, VIIb or VIIIb of the Periodic Table of Elements.

10 Claims, No Drawings

PREPARATION OF 1,4-BUTANEDIOL

CROSS-REFERENCE TO RELATED APPLICATION(S)

This is a Divisional Application of application Ser. No. 08/523,887, filed on Sep. 6, 1995, which stands allowed.

BACKGROUND OF THE INVENTION

The present invention relates to a process for the preparation of 1,4-butanediol by hydrogenation of 1,3-butadiene diepoxide.

1,4-Butanediol is an important chemical component for syntheses and is produced worldwide; it is used, for example, as a starting material for the synthesis of epoxy resins, polyesters, polyamides and polyurethanes. Traditionally, it is prepared by hydrogenation of 2-butyne-1,4-diol, which in turn is the product of a Reppe synthesis from acetylene and formaldehyde.

The catalytic hydrogenolysis of oxiranes has been described in many publications. An overview of the hydrogenolytic cleavage of oxiranes to alcohols over various hydrogenation catalysts is given, for example, in Houben-Weyl, Methoden der Organischen Chemie, Volume VI, 1a, Part 1, 1979, pages 338 to 342. Palladium, platinum and nickel catalysts are mentioned as conventional catalysts for the oxirane cleavage with hydrogenation.

Houben-Weyl, Methoden der Organischen Chemie, Volume VI, 3, 1965, pages 442 to 446, describes the catalytic hydrogenation of asymmetric 1,2-epoxides. As a rule for the regioselectivity of the cleavage of the three-membered ring, it is stated that in general cleavage takes place between the oxygen atom and the carbon atom which carries the smallest number of hydrogen atoms.

The catalytic hydrogenation of oxiranes with cleavage of a C—O bond is also described in Houben-Weyl, Methoden der Organischen Chemie, Volume IV, 1c, 1980, pages 374 to 377. Here, it is stated that the literature data on the direction of the ring cleavage in asymmetrically substituted oxiranes are in part contradictory. Nevertheless, in contradiction to the literature reference stated in the preceding paragraph, the rule formulated is that, where there is no activation by aryl or allyl groups in asymmetrically substituted oxiranes, the C—O bond cleaved is that which is least sterically shielded, ie. whose carbon atom carries the largest number of hydrogen atoms.

The catalytic hydrogenation of 1,3-butadiene diepoxide is novel. The contradictory statements with regard to the selectivity in the ring cleavage in asymmetrically substituted oxiranes in the prior art do not permit a prediction of the product to be expected, ie. 1,4-, 2,3- or 1,3-butanediol.

SUMMARY OF THE INVENTION

It is an object of the present invention to provide a route to 1,4-butanediol which avoids the Reppe synthesis and its unsafe catalysts and is nevertheless economical.

We have found that this object is achieved, according to the invention, by a process for the selective catalytic hydrogenation of 1,3-butadiene diepoxide to 1,4-butanediol, which comprises converting 1,3-butadiene diepoxide in the presence of hydrogen over a hydrogenation catalyst whose active component is not elemental palladium and/or platinum.

In the novel process, the surprisingly selective hydrogenolysis of the epoxide rings of 1,3-butadiene diepoxide takes place with formation of 1,4-butanediol according to the following equation:

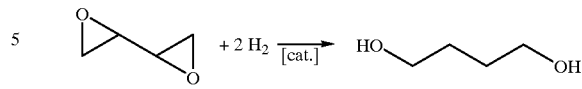

In carrying out the novel process, 1,3-butadiene diepoxide is converted into 1,4-butanediol in the presence of hydrogen and of a hydrogenation catalyst as defined above, usually at from 1 to 300, preferably from 10 to 250, in particular from 20 to 200, bar and at from 0 to 250° C., preferably from 60 to 220° C., particularly preferably from 100 to 200° C.

The novel process can be carried out without a solvent or advantageously in the presence of a solvent which is inert under the reaction conditions. Such solvents may be, for example, ethers, such as tetrahydrofuran, methyl tert-butyl ether or di-n-butyl ether, alcohols, such as methanol, ethanol, propanol, isopropanol, butanol, isobutanol or tert-butanol, hydrocarbons, such as petroleum ether, and N-alkyllactams, such as N-methylpyrrolidone or N-octylpyrrolidone.

In the novel process, the hydrogenation catalysts may be present in general in any form suitable for the hydrogenolysis of oxiranes. Thus, they may be hydrogenation catalysts which dissolve in the reaction medium to give a homogeneous solution, as described, for example, in Houben-Weyl, Methoden der Organischen Chemie, Volume IV/1c, pages 45 to 67.

In the novel process, however, heterogeneous hydrogenation catalysts are preferably used, ie. hydrogenation catalysts which are essentially insoluble in the reaction medium. Among these hydrogenation catalysts, preferred ones are those which contain one or more elements of the groups Ib, VIIb and VIIIb of the Periodic Table of Elements, in particular copper, rhenium, ruthenium, cobalt, rhodium, iridium, osmium and/or nickel.

Heterogeneous hydrogenation catalysts which may be used in the novel process are those which consist of metals in active, finely divided form having a large surface area, for example Raney nickel, Raney cobalt or rhenium sponge.

For example, precipitated catalysts may also be used in the novel process. Such catalysts can be prepared by precipitating their catalytically active components from their salt solutions, in particular from the solutions of their nitrates and/or acetates, for example by adding alkali metal and/or alkaline earth metal hydroxide and/or carbonate solutions, as, for example, sparingly soluble hydroxides, hydrated oxides, basic salts or carbonates, then drying the precipitates obtained and then converting them by calcination at in general from 300 to 700° C., in particular from 400 to 600° C., into the relevant oxides, mixed oxides and/or mixed-valency oxides, which are reduced by treatment with hydrogen or with hydrogen-containing gases at in general from 100 to 700° C., in particular from 150 to 400° C., to give the relevant metals and/or oxidic compounds of low oxidation states and thus converted into the actual, catalytically active form. As a rule, reduction is continued until water is no longer formed.

In the preparation of precipitated catalysts which contain a carrier, precipitation of the catalytically active components may be effected in the presence of the relevant carrier. However, the catalytically active components can advantageously also be precipitated simultaneously with the carrier from the relevant salt solutions.

The activation of both the precipitated catalysts and the supported catalysts can also be carried out in situ in the reaction mixture by the hydrogen present there, but activation is preferably effected separately before use.

The carriers used may be in general the oxides of aluminum and of titanium, zirconium dioxide, silica, kieselguhr, silica gel, aluminas, eg. montmorillonites, silicates, such as magnesium silicates or aluminum silicates, zeolites, such as ZSM-5 or ZBM-10 zeolites, or active carbon. Preferred carriers are aluminas, titanium dioxides, silicas, zirconium dioxides and active carbon. Mixtures of different carriers may of course also be used as carriers for the catalysts which can be used in the novel process.

The novel process can be carried out both continuously and batchwise. In the continuous procedure, it is possible to use, for example, tube reactors in which the catalyst is advantageously arranged in the form of a fixed bed, over which the reaction mixture can be passed by the liquid phase or trickle-bed procedure. In the case of the batchwise procedure, both simple stirred reactors and, advantageously, loop reactors may be used. Where loop reactors are used, the catalyst is advantageously arranged in the form of a fixed bed. The novel process can be carried out both in the gas phase and in the liquid phase.

The 1,3-butadiene diepoxide used as the starting material can be prepared, for example, by base-induced dehydrochlorination of dichlorobutanediols according to Przem. Chem. 56 (1977) 5, 246–50, or by dehydrobromination of 1,4-dibromobutanediol according to SU 1057-502-A. In the absence of halogen, butadiene diepoxide can be prepared, for example, by epoxidation of butadiene with hydrogen peroxide over a titanium silicalite as a catalyst, according to Chim. Ind. (Milan) 72 (7), 610–16, or according to EP 100 119 A. Furthermore, butadiene diepoxide can be prepared by epoxidation of butadiene with organic per acids according to JP 61072774 A or with cyclohexanone peroxide using titanium dioxide as a catalyst, according to EP 129 814. Finally, butadiene can be oxidized according to Zh. Obshch. Khim. 46 (6) (1976), 1420, with atmospheric oxygen at 250° C. in a tube reactor to give butadiene diepoxide.

DESCRIPTION OF THE PREFERRED EMBODIMENTS

Catalysts

In the unreduced state, the catalysts A to I used in the Examples have the compositions stated in Table I (data in % by weight):

TABLE I

| Catalyst | Preparation | Composition |
| --- | --- | --- |
| A | EP-A-100 406 | 67% CoO, 19% CuO, 7% $Mn_2O_3$, 3% $MoO_3$, 3% $H_3PO_4$, 0.2% $Na_2O$ |
| B | EP-A-382 049 | 10% CoO, 10% NiO, 4% CuO, 76% $Al_2O_3$ |
| C | US-A-5,037,793 | 50% NiO, 17% CuO, 31% $ZrO_2$, 2% $MoO_3$ |
| D | 1) | 1.5% Re, 3% Os, 1.5% $K_2O$, 94% C |
| E | EP-A-44 444 | 56% CuO, 44% $Al_2O_3$ |
| F | 2) | 22.3% CuO, 77.7% $SiO_2$ |
| G | 3) | 2% Ru, 98% $Al_2O_3$ |

TABLE I-continued

| Catalyst | Preparation | Composition |
| --- | --- | --- |
| H | 4) | 5% Pd, 95% C |
| I | 5) | 1% Pt, 99% $Al_2O_3$ |

Footnotes:
1) 4 mm active carbon extrudates were impregnated with an aqueous Re(VII) oxide solution, dried at 120° C. and treated with hydrogen at 250° C. The treated active carbon extrudates were then impregnated with an aqueous $K_2OsO_4$ hydrate solution, dried at 100° C./20 mbar and activated with hydrogen at 250° C.
2) 4 mm $SiO_2$ extrudates were impregnated with an ammoniacal copper carbonate solution, dried at 120° C., calcined at 350° C. and then milled to chips.
3) 1.5 mm $SiO_2$ extrudates were impregnated with an aqueous ruthenium hydrate solution, dried at 120° C. and calcined at 400° C.
4) 2 mm active carbon extrudates were impregnated with an aqueous palladium nitrate solution and dried at 100° C.
5) Source: Aldrich

EXAMPLE 1

In a 50 ml metal autoclave, 0.5 g of Raney cobalt was added to the solution to be hydrogenated, comprising 2.5 g of rac-1,3-butadiene diepoxide and 22.5 g of tetrahydrofuran, and hydrogenation was effected with hydrogen for 3 hours at 180° C. and 40 bar while stirring with a magnet stirrer. At a conversion of 98%, gas chromatographic analysis showed that 80 mol % of 1,4-butanediol and 19 mol % of n-butanol had been obtained.

EXAMPLE 2

The hydrogenation of 2.5 g of 1,3-butadiene diepoxide and 22.5 g of tetrahydrofuran was carried out as in Example 1, but over catalyst A instead of Raney cobalt. Catalyst A was first activated in a stream of hydrogen for 2 hours at 250° C. and then used in the form of 4 mm extrudates. At quantitative conversion, 81 mol % of 1,4-butanediol, 16 mol % of n-butanol and 3 mol % of 2,3-butanediol were found.

EXAMPLE 3

The hydrogenation of 2.5 g of 1,3-butadiene diepoxide and 22.5 g of tetrahydrofuran with 0.5 g of catalyst B was carried out as described in Example 1. Catalyst B was activated beforehand in a stream of hydrogen for 1 hour at 250° C. and used in the form of 4 mm extrudates. At a conversion of 100%, 77 mol % of 1,4-butanediol and 8 mol % of n-butanol were obtained.

EXAMPLE 4

The hydrogenation of 2.5 g of 1,3-butadiene diepoxide and 22.5 g of tetrahydrofuran with 0.5 g of Raney nickel was carried out at 140° C. and 40 bar in an apparatus as described in Example 1. After a reaction time of 4 hours and at quantitative conversion, the reacted mixture contained 74 mol % of 1,4-butanediol and 23 mol % of 2,3-butanediol.

EXAMPLES 5–9

The reaction conditions and the composition of the reacted mixture which were obtained in the hydrogenation of 2.5 g of 1,3-butadiene diepoxide and 22.5 g of tetrahydrofuran over, in each case, 0.5 g of the catalysts C–G at a total pressure of 40 bar are shown in Table II below.

Catalyst C was activated beforehand in a stream of hydrogen for 2 hours at 200° C. and then used in the form of 3 mm pellets.

Catalyst D had been prepared beforehand by activation in a of hydrogen for 1 hour at 150° C. and was used in the form of 4 mm extrudates.

Catalyst E was activated in a stream of hydrogen for 2 hours at 200° C. and then used in the form of 4 mm pellets.

Catalyst F was activated in the same way as catalyst E and then used in the form of 2–4 mm chips.

Catalyst G was activated beforehand in a stream of hydrogen for 1 hour at 250° C. and used in the form of 1.5 mm extrudates.

| Example | Catalyst | Reac. time [h] | T [° C.] | Conversion [%] | 1,4-BD | [mol %] 2,3-BD | n-BuOH |
|---|---|---|---|---|---|---|---|
| 5 | C | 1 | 180 | 97 | 64 | 16 | 8 |
| 6 | D | 4 | 180 | 88 | 57 | — | 11 |
| 7 | E | 4 | 140 | 98 | 53 | — | 45 |
| 8 | F | 4 | 140 | 99 | 30 | — | 42 |
| 9 | G | 4 | 180 | 97 | 31 | — | 10 |

1,4-butanediol, 1,2-BD: 2,3-butanediol, n-BuOH: n-butanol

COMPARATIVE EXAMPLE 1

The hydrogenation of 2.5 g of 1,3-butadiene diepoxide and 22.5 g of tetrahydrofuran was carried out with 0.5 g of catalyst H at 100° C. and 40 bar in an apparatus as described in Example 1. The catalyst was activated beforehand in a stream of hydrogen for 1 hour at 120° C. and used in the form of 2 mm extrudates. After a reaction time of 4 hours and at quantitative conversion, the reacted mixture contained 7 mol % of 1,4-butanediol and 82 mol % of 2,3-butanediol.

COMPARATIVE EXAMPLE 2

The hydrogenation of 2.5 g of 1,3-butadiene diepoxide and 22.5 g of tetrahydrofuran was carried out with 0.5 g of catalyst I at 180° C. and 40 bar in an apparatus as described in Example 1. The catalyst was used in powder form without activation. After a reaction time of 4 hours and at a conversion of 73%, the reacted mixture contained 1 mol % of 1,4-butanediol and 73 mol % of 2,3-butanediol.

We claim:

1. A process for the preparation of 1,4-butanediol, which comprises converting 1,3-butadiene diepoxide in the presence of hydrogen over a hydrogenation catalyst which comprises Ni and which may further comprise one or more elements selected from the group consisting of cobalt, copper, manganese, molybdenum, rhenium, osmium, ruthenium, rhodium and iridium.

2. The process defined in claim 1, wherein the hydrogenation catalyst is a heterogeneous hydrogenation catalyst.

3. The process defined in claim 2, wherein the hydrogenation catalyst comprises a carrier selected from the group consisting of oxides of aluminium and of titanium, zirconium dioxide, silica, kieselgur, silica gel, aluminas, silicates, zeolites and active carbon.

4. The process defined in claim 1, wherein the hydrogenation catalyst comprises a carrier selected from the group consisting of oxides of aluminium and of titanium, zirconium dioxide, silica, kieselgur, silica gel, aluminas, silicates, zeolites and active carbon.

5. The process defined in claim 1, which is carried out at from 0 to 300° C. and from 1 to 300 bar.

6. The process defined in claim 1, which is carried out in a solvent.

7. The process defined in claim 1, wherein the hydrogenation catalyst contains cobalt.

8. The process defined in claim 1, wherein the hydrogenation catalyst contains copper.

9. The process defined in claim 1, wherein the hydrogenation catalyst contains rhenium.

10. The process defined in claim 1, which is carried out at from 60 to 220° C. and from 10 to 250 bar.

* * * * *